(12) United States Patent
Hata

(10) Patent No.: US 10,703,913 B2
(45) Date of Patent: Jul. 7, 2020

(54) TITANIUM DIOXIDE POWDER AND COSMETIC FORMULATED THEREWITH

(71) Applicant: SHISEIDO COMPANY, LTD., Tokyo (JP)

(72) Inventor: Hideo Hata, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 23 days.

(21) Appl. No.: 16/065,965

(22) PCT Filed: Dec. 22, 2016

(86) PCT No.: PCT/JP2016/088579
§ 371 (c)(1),
(2) Date: Jun. 25, 2018

(87) PCT Pub. No.: WO2017/111136
PCT Pub. Date: Jun. 29, 2017

(65) Prior Publication Data
US 2018/0371257 A1 Dec. 27, 2018

(30) Foreign Application Priority Data

Dec. 25, 2015 (JP) .................................. 2015-254315

(51) Int. Cl.
*C09C 1/36* (2006.01)
*A61Q 1/02* (2006.01)
(Continued)

(52) U.S. Cl.
CPC ................ *C09C 1/363* (2013.01); *A61K 8/29* (2013.01); *A61Q 1/02* (2013.01); *A61Q 1/12* (2013.01);
(Continued)

(58) Field of Classification Search
CPC .. C09C 1/363; A61K 8/29; A61Q 1/02; A61Q 1/12; C01G 23/047; C01G 23/08
See application file for complete search history.

(56) References Cited

U.S. PATENT DOCUMENTS 4,668,501 A * 5/1987 Shibuta ................. C09C 1/3692
                                                   423/608
5,443,811 A    8/1995 Karvinen
(Continued)

FOREIGN PATENT DOCUMENTS

EP     0526712     6/1992
JP     4-214030    8/1992
(Continued)

OTHER PUBLICATIONS

EP 16879022.8, Extended European Search Report dated Jul. 16, 2019, 7 pages—English.
(Continued)

*Primary Examiner* — James A Fiorito
(74) *Attorney, Agent, or Firm* — Lackenbach Siegel, LLP; Andrew F. Young, Esq.

(57) ABSTRACT

A titanium dioxide powder has excellent red light-selective transmission function while maintaining hiding power. A cosmetic formulated therewith provides a natural finish and makes skin irregularities (pores) inconspicuous while having good covering properties. A titanium dioxide powder is obtained by firing titanium dioxide having acicular projections on the particle surface at 500-800° C. The titanium dioxide powder for the cosmetic is characterized by an apparent average particle size is 100-500 nm, an average crystallite size measured by X-ray diffraction is 15-30 nm, and a specific surface area is 10-30 m2/g.

4 Claims, 3 Drawing Sheets

(51) Int. Cl.
*A61Q 1/12* (2006.01)
*C01G 23/047* (2006.01)
*A61K 8/29* (2006.01)
*C01G 23/08* (2006.01)

(52) U.S. Cl.
CPC ........... *C01G 23/047* (2013.01); *C01G 23/08* (2013.01); *C01P 2002/60* (2013.01); *C01P 2002/70* (2013.01); *C01P 2004/62* (2013.01); *C01P 2006/12* (2013.01)

(56) References Cited

U.S. PATENT DOCUMENTS

| | | | |
|---|---|---|---|
| 5,536,448 | A | 7/1996 | Takahashi et al. |
| 6,099,634 | A | 7/2000 | Igarashi |
| 8,182,602 | B2 * | 5/2012 | Lamminmaki ........ B82Y 30/00 106/436 |
| 2009/0060856 | A1 | 3/2009 | Katsuyama et al. |
| 2010/0189666 | A1 | 7/2010 | Nakimura et al. |
| 2011/0192322 | A1 | 8/2011 | Lamminmaki et al. |

FOREIGN PATENT DOCUMENTS

| | | |
|---|---|---|
| JP | 7-138021 | 5/1995 |
| JP | 10-245228 | 9/1998 |
| JP | 2000-191325 | 7/2000 |
| JP | 2006-265134 | 10/2006 |
| JP | 2010-24180 | 2/2010 |
| JP | 2010-024189 | 2/2010 |
| JP | 2010-173863 | 8/2010 |
| JP | 2010-536689 | 12/2010 |

OTHER PUBLICATIONS

"Influence of Calcination Temperature on the Properties of Titanium Oxide Sulfur Recovery Catalysts", Ma, Guo, Hou, Huang, Han, Fang, State Key Laboratory of Coal conversion, Institute of Coal Chemistry, Chinse Academy of Sciens, Talyuan 030001, P.R. China, Copyright 2014 American Scientific Publishers, Journal of Nanoscience an Nanotechnology, vol. 14, 7181-7188, 2014, www.aspbs.com/jon, 7 pages.
"Influence of calcinations parameters on the $TiO_2$ photocatalytic properties", Luis, Neves, Mendonca, Monteiro, University of Lisbon, University of Avelro, University of Lisbon, Materials Chemistry and Physics, 125 (2011) 20-25 Journal homepage: www.elsevier.com/locate/matchemphys, 6 pages.
CN Appln. No. 2016800761052, First Examination Opinion Notice, dated Sep. 9, 2019, 8 pages—Chinese, 15 pages—English.
Preparation of Nano Rutile Titania Powders with High Photocatalytic Preoperties, Sun, Gao, Zhang, State Key Laboratory of High Performance Ceramics and Superfine Microstructure, Shanghai Institute of Cerami cs, Chinese Academy of Sciences, Shanghai 200050, dated Sep. 27, 2002, 4 pages Chinese, 2 pages—English + English Abstract.
PCT/JP2016/088579 Written Opinion and International Search Report, dated Feb. 21, 2017, 12 page—English, 9 pages—Japanese.

* cited by examiner

TITANIUM DIOXIDE POWDER AND COSMETIC FORMULATED THEREWITH

CROSS REFERENCE TO PRIORITY CLAIM

This application claims the priority of a § 371 national phase of Ser. No.:PCT/JP2016/088579 filed Dec. 22, 2016, the entire contents of which are incorporated herein by reference which in turn claims priority from Japanese Patent Application No. 2015-254315 filed on Nov. 25, 2015, which is incorporated herein by reference.

RELATED APPLICATIONS

This application claims the priority of Japanese Patent Application No. 2015-254315 filed on Nov. 25, 2015, which is incorporated herein by reference.

TECHNICAL FIELD

The present invention relates to a titanium dioxide powder, more particularly, to a titanium dioxide powder which can be suitably used for, for example, cosmetics, paints, and catalysts, and to a cosmetic containing the titanium dioxide powder.

BACKGROUND ART

A titanium dioxide has a high-refractive index and excellent whiteness, hiding power, and tinting power, and has therefore been widely used as a white pigment for paints, plastics, and the like. Further, the titanium dioxide can also be used for, for example, cosmetics and catalysts as a substance for shielding ultraviolet rays such as an ultraviolet ray absorbing agent or an ultraviolet ray shielding agent by controlling a particle size or photoactivity of the titanium dioxide. For that reason, in recent years, research and development has been actively conducted on such use of the titanium dioxide.

It has been known that when a titanium dioxide powder having an apparent specific average particle size, which comprises small spherical particles of a titanium dioxide having a specific average primary particle size and a spherical moss-like shape made up of a large number of titanium dioxide, is used for cosmetics, the titanium dioxide powder serves as a functional material capable of imparting a good slippery property and excellent light fastness that conventional titanium dioxides do not have (Patent Literature 1).

Further, a cosmetic for lips containing 1 to 15% by mass of rutile titanium oxide aggregated particles having an average particle size of 0.2 to 0.4 μm and an average coefficient of friction (MIU value) of 0.4 to 0.6 and 1 to 40% by mass of semisolid oil has been known to give luster, cover noticeable wrinkles of lips, and provide excellent long-lasting makeup properties (Patent Literature 2).

Moreover, it has been known that a cosmetic containing a coloring material having a small absorbance of light on a long wavelength side (wavelength of 630 to 700 nm) in a visible light region makes the skin look close to the bare skin due to a light transmitting property inside of the skin, and thus a natural makeup finish can be achieved (Patent Literature 3).

While the titanium dioxide has a high-refractive index and high-hiding power to hide pigmented spots and the like of the skin, blending a large amount of titanium dioxides to increase the hiding power results in providing an unnatural makeup finish (effect) and thus irregularities on the skin may become more noticeable as compared to those on the bare skin before application. This is because as the bare skin has a light transmitting property and has a large amount of light scattered and/or fed back from inside the skin, as described above, shadows are unlikely to be created on tiny irregularities on the skin and that makes the skin look natural. However, as the titanium dioxide reflects a much larger amount of light by its surface, light is prevented from transmitting inside the skin and thus shadows are created on the irregularities on the skin, which makes the irregularities on the skin noticeable. For that reason, it is desired to develop a titanium oxide designed to further improve the transmitting property of light on the long wavelength side while having the hiding power equivalent to a commonly-used titanium oxide pigment.

As described above, as the titanium oxide having an improved light transmittance for light on the long wavelength side, a rutile titanium oxide in the shape of strips or straw bundles has been developed which has a particulate form formed by bundle-like orientation and aggregation of rod-shaped particles, where the formed particle has an apparent average length of 80 to 300 nm, an apparent average width of 30 to 150 nm, an apparent average axial ratio represented by the apparent average length/the apparent average width of 1.1 to 4, and a specific surface area of 120 to 180 m$^2$/g. This titanium oxide has been known to have a high-level of transparency and ultraviolet ray shielding performance (Patent Literature 4).

However, because this titanium dioxide is an aggregate of rod-shaped particles and has many voids in the secondary aggregate, the titanium dioxide has a decreased apparent refractive index and thus an insufficient hiding power when it is actually added to cosmetics. And because the titanium dioxide is intended mainly for ultraviolet protection, the secondary aggregate has an apparent particle size of less than 100 nm, which is clearly smaller than the particle size capable of maximizing the scattering effect of the titanium oxide based on Mie theory, and this is also a factor making the hiding power low.

PRIOR ART DOCUMENTS

Patent Literatures

[Patent Literature 1] Japanese Unexamined Patent Publication No. 2000-191325
[Patent Literature 2] Japanese Unexamined Patent Publication No. 2010-24189
[Patent Literature 3] Japanese Unexamined Patent Publication No. 2006-265134
[Patent Literature 4] Japanese Unexamined Patent Publication No. 2010-173863

SUMMARY OF THE INVENTION

Problem to be Solved by the Invention

The present invention has been made in view of the conventional art. It is an object of the present invention to provide a titanium dioxide having excellent function of transmitting more light in a long wavelength region (red light selective transmission function) while retaining hiding power.

Solution to Problem

The present inventors have conducted an extensive research to solve the problem and consequently found that a titanium dioxide that is produced by calcining a particular titanium dioxide to give a particular particle size, a particular crystallite size, and a particular specific surface area has sufficient hiding power required for cosmetics and shows excellent red light selective transmission function. Based on the above findings, the present inventors have completed the present invention.

That is, a titanium dioxide powder according to the present invention is produced by calcining a rutile titanium dioxide having needle-shaped projections on the particle surface, and the titanium dioxide powder has an apparent average particle size of 100 to 500 nm, an average crystallite size measured by X-ray diffraction of 15 to 30 nm, and a specific surface area of 10 to 30 m$^2$/g.

The titanium dioxide powder according to the present invention is a rutile titanium dioxide powder having an average crystallite size measured by X-ray diffraction of 15 to 30 nm, a specific surface area of 10 to 30 m$^2$/g, a reflectance at 450 nm 1.3 times or more as high as the reflectance at 650 nm, and a color difference ($\Delta E$) of 20 or less.

As for the color difference ($\Delta E$), the titanium dioxide powder was dispersed and mixed into a nitrocellulose lacquer in a concentration of 5%. A resultant dispersion was applied to a black-and-white hiding power test chart in accordance with JIS-K5400 at a coating thickness of 0.101 μm and dried to prepare a test sample. Using the prepared test sample, a colorimetric measurement was performed on each coating surface of a black portion and a white portion of the chart with a spectrocolorimeter. The color difference ($\Delta E$) was calculated based on Hunter Lab color space.

In the titanium dioxide powder, a calcination temperature for the titanium dioxide is preferably 500° C. to 700° C.

In the titanium dioxide powder, a calcination temperature for the titanium dioxide is preferably 600° C. to 700° C.

The titanium dioxide powder preferably has the reflectance at 450 nm 1.3 times or more as high as the reflectance at 650 nm, and transmits more light on a long wavelength side.

It is preferable that the surface of the titanium dioxide powder is treated.

A cosmetic according to the present invention contains the titanium dioxide powder.

A method for producing the rutile titanium dioxide powder of the present invention includes a step of calcining a rutile titanium dioxide having needle-shaped projections on the particle surface, and the rutile titanium dioxide powder that is produced thereby has an apparent average particle size of 100 to 500 nm, an average crystallite size, measured by X-ray diffraction, of 15 to 30 nm and a specific surface area of 10 to 30 m$^2$/g.

In the method for producing the titanium dioxide powder, a calcination temperature for the titanium dioxide is preferably 500° C. to 700° C.

The titanium dioxide powder according to the present invention is preferably the rutile titanium dioxide powder produced by calcining a rutile titanium dioxide having needle-shaped projections on the particle surface and satisfying the following (a) to (c).
(a) An apparent average particle size of 100 to 600 nm
(b) An average crystallite size measured by X-ray diffraction of 1 to 25 nm
(c) A specific surface area of 40 to 200 m$^2$/g That is, the titanium dioxide powder according to the present invention is the rutile titanium dioxide powder produced by calcining a rutile titanium dioxide having needle-shaped projections on the surface of a particle which is formed by orientation and aggregation of rod-shaped or needle-shaped particles, and it preferably has an apparent average particle size of 100 to 500 nm, an average crystallite size measured by X-ray diffraction of 15 to 30 nm, and a specific surface area of 10 to 30 m$^2$/g.

Advantageous Effects of Invention

According to the present invention, the titanium dioxide powder having excellent red light selective transmission function while improving the hiding power is provided.

DESCRIPTION OF EMBODIMENTS

Figure 1:
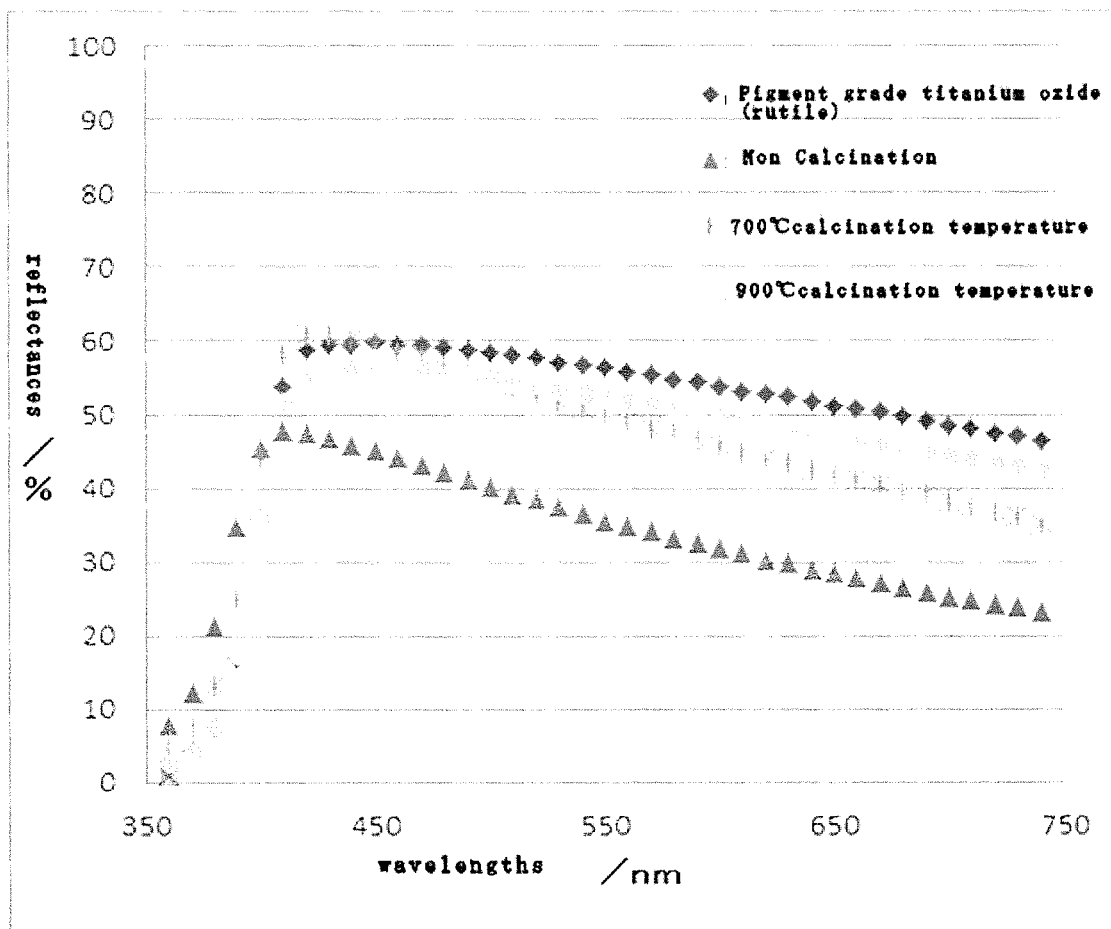
FIG. 1 shows a spectral reflectance for a rutile pigment grade titanium oxide (*1), Titanium oxide B (not calcined), and Titanium oxide B calcined at 700 and 900° C.

A titanium dioxide powder according to the present invention is the titanium dioxide powder produced by calcining, at a temperature ranging from 500 to 800° C., more preferably from 550 to 750° C., a titanium dioxide having needle-shaped projections on the surface of a particle which is formed by orientation and aggregation of rod-shaped or needle-shaped particles, and the product titanium dioxide has an average crystallite size measured by X-ray diffraction of 15 to 30 nm, an apparent average particle size of the titanium dioxide of 100 to 500 nm, more preferably 200 to 400 nm, and a specific surface area of 10 to 30 m$^2$/g.

(Titanium Dioxide Used as Mother Nucleus)

The crystalline form of titanium dioxide used as a mother nucleus include anatase and rutile by crystal structure. The crystalline form of titanium dioxide used in the present invention needs to be rutile which has high-hiding power since the rutile has a low-photocatalytic activity and a high-refractive index.

As a rutile titanium dioxide used as a mother nucleus, the titanium dioxide having a function of transmitting red light is used. An apparent average particle size of the titanium dioxide used as a mother nucleus is not limited to a particular size. However, considering that a shrinkage phenomenon usually takes place after calcination, it is desired that the apparent average particle size is 100 to 600 nm, more preferably 200 to 500 nm in terms of achieving the hiding power by light scattering of the titanium dioxide and excellent capability of transmitting red-color obtained in the present invention.

The rutile titanium dioxide used as a mother nucleus may be in the shape of straw bundle, strip, sphere, needle, rod or the like.

A specific surface area of the titanium dioxide used as a mother nucleus is not limited to a particular dimension, and it is desired that the specific surface area is 40 to 200 m$^2$/g in terms of an apparent refractive index which is efficiently improved by the calcination.

The rutile titanium dioxide used as a mother nucleus is not limited to a particular kind and is preferably the one having an average crystallite size measured by X-ray diffraction of 1 to 25 nm.

The titanium dioxide used as a mother nucleus may be a commercially-available product. Examples thereof include an ST-700 series manufactured by Titan Kogyo, Ltd. Among the ST-700 series, ST-710 and ST-730 may be used.

(Titanium Dioxide Powder of the Present Invention)

The titanium dioxide powder of the present invention is produced by calcining the titanium dioxide used as a mother nucleus.

A calcination temperature cannot be unconditionally defined as it depends on a device performing the calcination. However, it is desired that a temperature condition is set so that voids between rod-shaped or needle-shaped particles, which are primary particles existing prior to the calcination having rod-shaped or needle-shaped particles being oriented and aggregated, are reduced and an average crystallite size measured by X-ray diffraction is not excessively increased due to sintering of the rod-shaped or needle-shaped particles. Such a temperature condition allows both the sufficient hiding power and the red light selective transmission function to be obtained.

An appropriate calcination temperature is varied depending on the calcination device. When the calcination is performed in a muffle furnace or a rotary kiln which is a commonly-used calcining furnace, it is desired that the calcination is performed at a temperature ranging from 500 to 800° C., more preferably from 550 to 750° C. When the temperature is below 500° C., the hiding power is insufficient as voids existed prior to the calcination are not sufficiently reduced. When the temperature exceeds 800° C., the red light selective transmission function is lost as the sintering proceeds excessively.

The titanium dioxide of the present invention needs to have the average crystallite size measured by X-ray diffraction of 15 to 30 nm.

When the crystallite size is less than 15 nm, it is not preferable because the sufficient hiding power cannot be obtained. Additionally, when the crystallite size is more than 30 nm, it is not preferable because the sufficient red light selective transmission function is lost as the sintering proceeds.

Further, the titanium dioxide powder of the present invention needs to have the apparent average particle size of 100 to 500 nm, more preferably 200 to 400 nm, in terms of efficiently achieving the hiding power due to the light scattering and excellent red-color transmission function.

The specific surface area of the titanium dioxide powder of the present invention is an index that shows a reduction in voidage and a progression of the sintering of the obtained titanium oxide particles, and it needs to be 10 to 30 $m^2/g$. The specific surface area of less than 10 $m^2/g$ is not preferable because the sintering proceeds and the sufficient red light selective transmission function is eventually lost. Additionally, the specific surface area of more than 30 $m^2/g$ is not preferable because too many voids exist and consequently the sufficient hiding power cannot be achieved.

The titanium dioxide powder of the present invention can be surface treated after the calcination. Performing surface treatment can improve long-lasting makeup properties involving viscosity, dispersibility to oil, and water repellency, and at the same time, produce a titanium dioxide that is excellent in usability.

Examples of an inorganic substance which can be used as a surface treatment agent include a hydrous oxide or oxide of metal such as aluminum, silicon, zinc, titanium, zirconium, iron, cerium, and tin. The metallic salt to be used is not limited to a particular substance.

Examples of an organic substance, which can be used as a surface treatment agent after surface treatment with metal oxide or hydroxide such as aluminum hydroxide or oxide, and is intended to impart a lipophilic property, include fatty acids such as stearic acid, oleic acid, isostearic acid, myristic acid, palmitic acid, and behenic acid, silicone compounds such as methylhydrogenpolysiloxane, dimethicone, alkyl (C8-C18 or the like)trialkoxysilane, amino-modified silicone, and carboxyl-modified silicone, fluorine compounds such as perfluoroalkyl alkyl phosphate, dextrin myristate, dextrin palmitate, and amino acid derivatives such as lauroyl lysine, lauroyl glutaminate, or the like.

It is preferable that these surface treatment agents are contained in an amount of 1 to 10% by mass relative to the titanium dioxide powder so that high hiding power is obtained.

The titanium dioxide powder of the present invention can be widely blended in cosmetics, pigments, inks, and paints, for example.

The composition of the present invention can be in any form, and the examples include a powder form, cream form, lotion form, lotion form, oily form, paste form.

Examples of intended uses of cosmetic include makeup cosmetic such as makeup base, foundation, concealer, face powder, control color, sunscreen cosmetic, lipstick, lip cream, eye shadow, eye-liner, mascara, cheek color, manicure, body powder, perfume powder, baby powder, skincare cosmetic, and haircare cosmetic.

In the cosmetic of the present invention, in addition to the above-described components, according to the intended use, the other components can be blended within the weight and quality range which the effect of the present invention is not impaired.

EXAMPLES

The present invention will be further described in detail in the following Examples. However, the present invention is not particularly limited to the following Examples. Unless otherwise noted, the blending amount of each component will be expressed in % by mass relative to a system containing the component.

Before describing Examples, test evaluation methods used in the present invention will be described.

Evaluation (1): Method for Measuring Average Crystallite Size

A sample was measured using an X-ray diffractometer (Geigerflex, manufactured by Rigaku Corporation), and an average crystallite size of the sample was calculated by employing Scherrer equation.

Evaluation (2): Evaluation of Hiding Power

A titanium dioxide powder was dispersed and mixed into a nitrocellulose lacquer in a concentration of 5%. A resultant dispersion was applied to a black-and-white hiding power test chart in accordance with JIS-K5400 with a coating thickness of 0.101 μm and dried to prepare a test sample. Using the prepared test sample, a colorimetric measurement was performed on each coating surface of a black portion and a white portion of the chart with a spectrocolorimeter (CM-2600, manufactured by Konica Minolta, Inc.). A color difference (ΔE) was calculated based on Hunter Lab color space and used it for evaluating the hiding power. Note that the higher the ΔE, the lower the hiding power is; and the lower the ΔE, the higher the hiding power.

$$\Delta E = \sqrt{(L1-L2)^2 + (a1-a2)^2 + (b1-b2)^2}$$

(Evaluation Criteria)
A: $\Delta E \leq 20$
B: $20 < \Delta E \leq 25$
C: $25 < \Delta E \leq 30$
D: $30 < \Delta E$ Evaluation (3): Evaluation of Red-Color Transmitting Property Among spectral reflectances at individual wavelengths measured on the black portion of the chart, as for the hiding power described above, the reflectances at two wavelengths of 450 nm and 650 nm were used to calculate their ratio, R450/R650 where R450 denotes the reflectance at a wavelength of 450 nm and 650 denotes the average reflectance at 650 nm, the ratio representing red-color transmitting property.

The higher the calculated value of R450/R650, the higher the red-color transmitting property, and the lower the calculated value of R450/R650, the lower the calculated value of R450/R650.

(Evaluation Criteria)
AA: $1.4 < R450/R650$
A: $1.35 < R450/R650$
B: $1.3 < R450/R650 \leq 1.35$
C: $1.2 < R450/R650 \leq 1.3$
D: $R450/R650 \leq 1.2$ Evaluation (4): Method for Measuring Specific Surface Area The specific surface area per unit mass can be determined by a nitrogen adsorption method known as the BET (Brunauer-Emmett-Teller) method described in The Journal of the American Chemical Society, vol. 60, p.309, February 1938 which corresponds to the ISO international standard 5794-1 (Appendix D)

First, the present inventors used commercially available pigment grade rutile and anatase titanium oxides and evaluated them using the above evaluation methods. The results are shown in Table 1.

TABLE 1

| | Test example | |
|---|---|---|
| | 1<br>Pigment grade titanium oxide (rutile) *1 | 2<br>Pigment grade titanium oxide (anatase) *2 |
| Hiding power ($\Delta E$(Hunter)) | 16.1 | 21.4 |
| Evaluation of hiding power | A | B |
| R450/R650 | 1.18 | 1.14 |
| Evaluation of red-color transmitting property | D | D |
| Specific surface area m²/g | 5 | 6 |
| Crystal particle diameter (nm) | 55 | 59 |

*1: Tipaque CR-50 (manufactured by Ishihara Sangyo Kaisha, Ltd., apparent average particle size: 200 nm, form: indefinite form)
*2: Bayer titanium A (manufactures by Bayer AG, apparent average particle size: 400 nm, form: indefinite form)

Both the rutile pigment grade titanium oxide and the anatase pigment grade titanium oxide showed a low red-color transmitting property. Even when these titanium oxides were calcined under high-temperature conditions, the red-color transmitting property was poor.

The present inventors conducted a study on the possibility of producing a titanium dioxide having an excellent red-color transmitting property by using a rutile titanium oxide having high-hiding power.

The present inventors used the method according to Patent Literature 4 and synthesized two kinds of titanium dioxide having different particle sizes and having needle-shaped projections on the particle surface where needle-shaped particles are oriented and aggregated.

The resultant titanium oxides were called Titanium oxide A (apparent average particle size: 0.2 to 0.3 μm, with needle-shaped projections) and Titanium oxide B (apparent average particle size: 0.3 μm, with needle-shaped projections), respectively.

Titanium dioxide having needle-shaped projections on the particle surface which was commercially available (ST-730, manufactured by Titan Kogyo, Ltd.) was called Titanium oxide C (apparent average particle size: 0.5 with needle-shaped projections)

The following method was performed on each titanium dioxide to produce a titanium dioxide powder. The produced titanium dioxide powder was evaluated using the above evaluation methods and studied regarding a relationship between a kind of titanium dioxide before the calcination and a calcination temperature. The results are shown in Table 2 to Table 4.

The measurement results of a spectral reflectance of the rutile pigment grade titanium oxide (*1) and Titanium oxide B (not calcined, calcination temperature: 700° C., 900° C.) were shown in FIG. 1. The measurement was performed in such a manner that the titanium dioxide powder was dispersed and mixed into a nitrocellulose lacquer in a concentration of 5%, a resultant dispersion was applied to black and white hiding power test charts in accordance with JIS-K5400 with a coating thickness of 0.101 μm and dried to prepare test samples, and using the prepared test samples, a colorimetric measurement was performed on each coating surface of a black portion of the charts with a spectrocolorimeter (CM-2600, manufactured by Konica Minolta, Inc.) to give the spectral reflectance.

(Method for Producing Titanium Dioxide Powder)

100 g of a titanium dioxide was placed in a crucible made of quartz, which was calcined at each temperature for 1 hour in a muffle furnace to produce a titanium dioxide powder.

Titanium Oxide A (Apparent Average Particle Size: 0.2 to 0.3 μm, Needle-Shaped Projection Form)

TABLE 2

| | Test example | | | | | |
|---|---|---|---|---|---|---|
| | 1-1 | 1-2 | 1-3 | 1-4 | 1-5 | 1-6 |
| Calcination temperature | 0 | 300 | 500 | 700 | 800 | 900 |
| Hiding power ($\Delta E$(Hunter)) | 33.9 | 26.2 | 22.7 | 19.9 | 18.3 | 17.6 |
| Evaluation of hiding power | D | C | B | A | A | A |
| R450/R650 | 1.58 | 1.45 | 1.43 | 1.42 | 1.29 | 1.14 |
| Evaluation of red-color transmitting property | AA | AA | AA | AA | C | D |
| Specific surface area m²/g | 101 | 62 | 32 | 14 | 13 | 5 |

Titanium Oxide B (Apparent Average Particle Size: 0.3 μm, Needle-Shaped Projection Form)

TABLE 3

|  | Test example | | | | | |
| --- | --- | --- | --- | --- | --- | --- |
|  | 2-1 | 2-2 | 2-3 | 2-4 | 2-5 | 2-6 |
| Calcination temperature | 0 | 300 | 500 | 700 | 800 | 900 |
| Hiding power (ΔE(Hunter)) | 34.0 | 25.2 | 21.7 | 18.8 | 16.8 | 17.2 |
| Evaluation of hiding power | D | C | B | A | A | A |
| R450/R650 | 1.57 | 1.48 | 1.42 | 1.40 | 1.31 | 1.19 |
| Evaluation of red-color transmitting property | AA | AA | AA | AA | B | D |
| Specific surface area m$^2$/g | 117 | 68 | 30 | 18 | 15 | 6 |

Titanium Oxide C (Apparent Average Particle Size: 0.5 μm, Needle-Shaped Projection Form)

TABLE 4

|  | Test example | | | | | |
| --- | --- | --- | --- | --- | --- | --- |
|  | 3-1 | 3-2 | 3-3 | 3-4 | 3-5 | 3-6 |
| Calcination temperature | 0 | 300 | 500 | 700 | 800 | 900 |
| Hiding power (ΔE(Hunter)) | 34.8 | 25.9 | 23.2 | 19.6 | 19.3 | 19.1 |
| Evaluation of hiding power | D | C | B | A | A | A |
| R450/R650 | 1.45 | 1.33 | 1.31 | 1.19 | 1.13 | 1.09 |
| Evaluation of red-color transmitting property | AA | B | B | D | D | D |
| Specific surface area m$^2$/g | 98 | 56 | 27 | 10 | 9 | 6 |

Titanium oxides A to C showed an improved hiding power when the calcination temperature was increased. The specific surface area was decreased as the temperature rose, which tells that the voids existing in the particle were reduced. This led to an improvement of an apparent refractive index and the hiding power was eventually improved. However, the red-color transmitting property was gradually deteriorated. When the calcination was performed especially under high temperature conditions, sintering definitely took place and an initial red-color transmitting property was significantly deteriorated.

In particular, for Titanium oxide C having a large particle size, the red-color transmitting property was almost lost at 700° C.

In terms of improving the hiding power and retaining the red-color transmitting property, Titanium oxide B showed an ability to tolerate under a wide range of temperatures.

Figure 2:
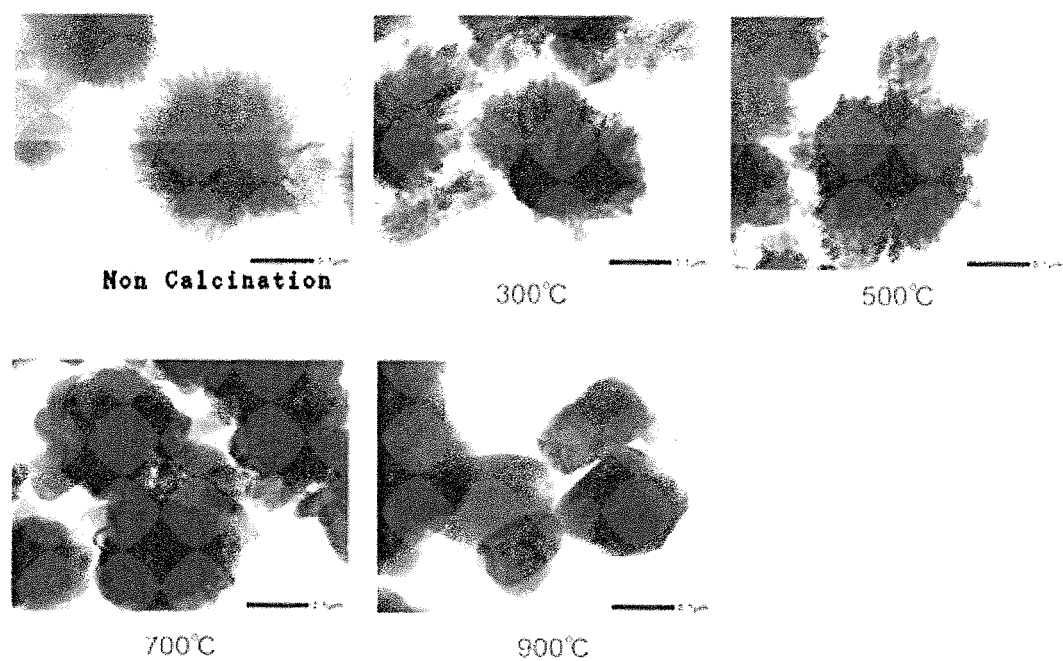
FIG. 2 is TEM observation showing a change in shape of Titanium dioxide B at each calcination temperature.

Photographs of a non-calcined and calcined Titanium dioxide B (calcination temperature: 300° C., 500° C., 700° C., 900° C.) were taken. The results are shown in FIG. 2.

Figure 3:
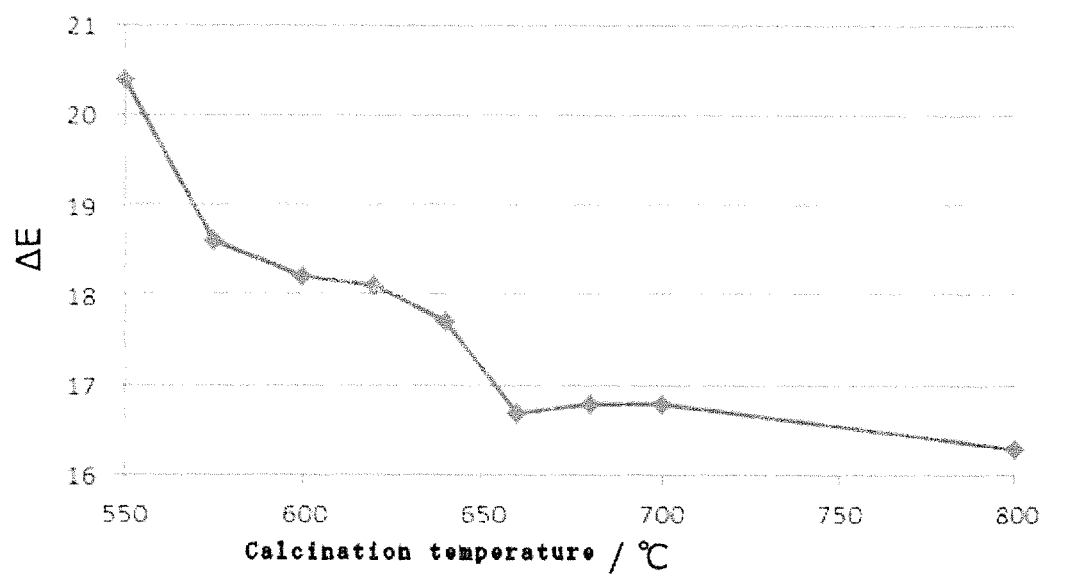
FIG. 3 shows a change in hiding power of Titanium oxide B according to a change in the calcination temperature of a rotary kiln.
Figure 4:
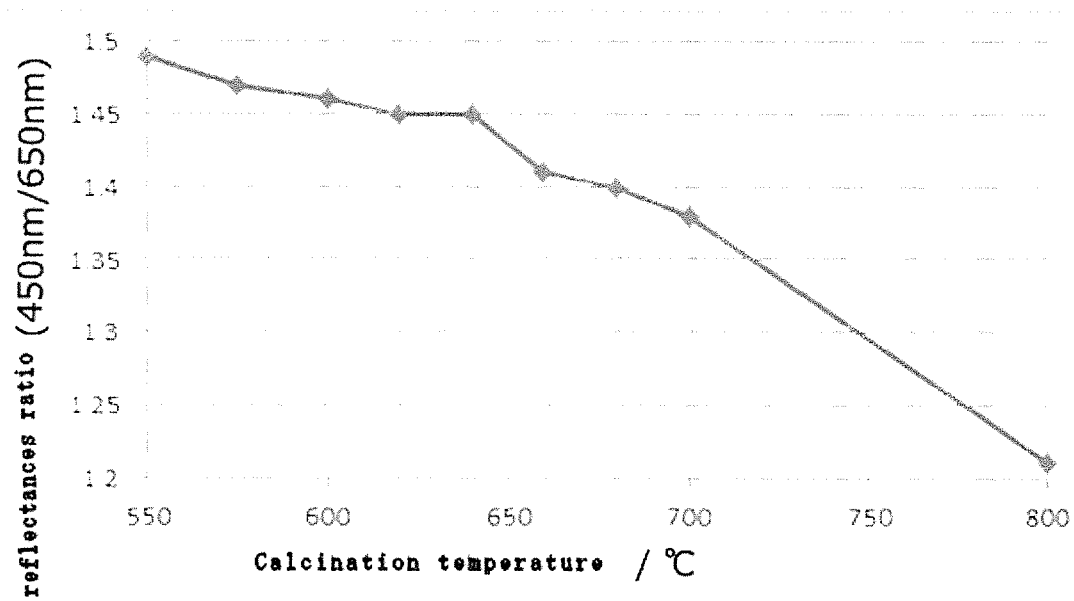
FIG. 4 shows a change in a red-color transmitting property according to a change in the calcination temperature of Titanium oxide B according to a change in the calcination temperature of the rotary kiln.

Further, the hiding power and the red-color transmitting property of Titanium dioxide B according to a change in the calcination temperature of the rotary kiln were measured. Each of the measurement results are shown in FIG. 3 and FIG. 4.

Based on the above results, when the calcination is performed in the muffle furnace, it is desirable that an appropriate temperature range is from 500 to 800° C., particularly from 500 to 700° C.

Next, the present inventors conducted a study on the calcination temperature ranging from 500° C. to 800° C. in detail using Titanium oxide B as a mother nucleus. That is, the present inventors evaluated a dioxide powder calcined at various calcination temperatures using the above evaluation methods. The results are shown in Table 5 and Table 6.

The calcination was performed in a rotary calcining furnace (rotary kiln) which allows a production close to a mass production with high calcination efficiency.

It is known that the rotary calcining furnace generally has high-calcination efficiency and can provide the same calcination state as the calcination performed in a static muffle furnace, with a lower temperature.

TABLE 5

|  | Calcination temperature | | | | | |
| --- | --- | --- | --- | --- | --- | --- |
|  | 0 | 550 | 575 | 600 | 620 | 640 |
| Average crystallite size nm | 11 | 17 | 19 | 20 | 21 | 22 |
| Specific surface area | 117 | 21 | 20 | 18 | 18 | 17 |
| Hiding power (ΔE(Hunter)) | 34.0 | 20.4 | 18.6 | 18.2 | 18.1 | 17.7 |
| Evaluation of hiding power | D | B | A | A | A | A |
| R450/R650 | 1.57 | 1.49 | 1.47 | 1.46 | 1.45 | 1.45 |
| Evaluation of red-color transmitting property | AA | AA | AA | AA | AA | AA |

TABLE 6

|  | Calcination temperature | | | |
| --- | --- | --- | --- | --- |
|  | 660 | 680 | 700 | 800 |
| Average crystallite size nm | 24 | 27 | 29 | 33 |
| Specific surface area | 16 | 15 | 14 | 9 |
| Hiding power (ΔE(Hunter)) | 16.7 | 16.8 | 16.8 | 16.3 |
| Evaluation of hiding power | A | A | A | A |
| R450/R650 | 1.41 | 1.4 | 1.38 | 1.21 |
| Evaluation of red-color transmitting property | AA | A | A | C |

Based on these results, it was found that in order to obtain excellent hiding power and red-color transmitting property, the calcination temperature is preferably 550 to 700° C., more preferably 575 to 660° C.

Further, the present inventors used the titanium dioxide of the present invention that has been produced at the calcination temperature of 660° C. in Table 6 to prepare, in a usual manner, a powdered cosmetic and a water-in-oil type emulsified cosmetic each containing a hydrophobized titanium dioxide that has been produced using the surface treatment method below. The produced cosmetics were evaluated using the evaluation method below. The results of the powdered cosmetic and the water-in-oil type emulsified cosmetic were shown in Table 7 and Table 8, respectively.

(Surface Treatment Method of Titanium Dioxide Powder)

The produced titanium dioxide powder was dispersed in ion-exchanged water, which was heated and then made to adsorb 3% by mass of stearic acid. After that, the resultant was dehydrated, washed, and dried to produce a surface-treated titanium dioxide.

Evaluation (5): Covering of Pigmented Spots and Freckles 10 trained-expert panelists applied the sample to their faces and evaluated an impression of use upon application.
A: 9 or more out of 10 panelists answered that pigmented spots and freckles were covered.

B: 7 or more to less than 9 out of 10 panelists answered that pigmented spots and freckles were covered.
C: 5 or more to less than 7 out of 10 panelists answered that pigmented spots and freckles were covered.
D: less than 5 out of 10 panelists answered that pigmented spots and freckles were covered.

Evaluation (6): Unnoticeableness of Pores 10 trained-expert panelists applied the sample to their faces and evaluated an impression of use upon application.
A: 9 or more out of 10 panelists answered that pores were unnoticeable.
B: 7 or more to less than 9 out of 10 panelists answered that pores were unnoticeable.
C: 5 or more to less than 7 out of 10 panelists answered that pores were unnoticeable.
D: less than 5 out of 10 panelists answered that pores were unnoticeable.

Evaluation (7): Natural Makeup Finish 10 trained-expert panelists applied the sample to their faces and evaluated an impression of use upon application.
A: 9 or more out of 10 panelists answered that a natural makeup finish was obtained.
B: 7 or more to less than 9 out of 10 panelists answered that a natural makeup finish was obtained.
C: 5 or more to less than 7 out of 10 panelists answered that a natural makeup finish was obtained.
D: less than 5 out of 10 panelists answered that a natural makeup finish was obtained.

Evaluation (8): No Powderiness 10 trained-expert panelists applied the sample to their faces and evaluated an impression of use upon application.
A: 9 or more out of 10 panelists answered that it was not powdery.
B: 7 or more to less than 9 out of 10 panelists answered that it was not powdery.
C: 5 or more to less than 7 out of 10 panelists answered that it was not powdery.
D: less than 5 out of 10 panelists answered that it was not powdery.

Powder Cosmetic

Water-in-Oil Emulsion Cosmetic

TABLE 8

|  | Example | | |
|---|---|---|---|
|  | 2-1 | 2-2 | 2-3 |
| Dimethicone 1.5 cs | 20 | 20 | 20 |
| Trimethylsiloxy silicate | 2.5 | 2.5 | 2.5 |
| Decamethyl cyclopentasiloxane | 5 | 5 | 5 |
| Dimethicone 6 cs | 3 | 3 | 3 |
| Cethyl octanoate | 3 | 3 | 3 |
| Octyl methoxycinnamate | 3 | 3 | 3 |
| PEG-10 dimethicone | 2 | 2 | 2 |
| Lauryl PEG-9 polydimethylsiloxyethyl dimethicone | 2 | 2 | 2 |
| Sorbitan sesquiisostearate | 0.8 | 0.8 | 0.8 |
| Distearyl dimethyl ammonium-modified hectorite | 0.5 | 0.5 | 0.5 |
| Stearic acid-treated fine particle titaniun oxide | 3 | 3 | 3 |
| Methicone-treated fine particle titamiun oxide | 2 | 2 | 2 |
| Stearic acid-treated pigment grade titaniun oxide | 10 | — | — |
| Stearic acid-treated titanium dioxide (The present invention) | — | 10 | 13 |
| Silicone-treated yellow iron oxide | 2 | 2 | 2 |
| Silicone-treated colcothar | 0.6 | 0.6 | 0.6 |
| Silicone-treated black iron oxide | 0.1 | 0.1 | 0.1 |
| Spherical polymethyl silsesquioxane | 2 | 2 | 2 |
| Ion-exchanged water | Balance | Balance | Balance |
| Dipropylene glycol | 5 | 5 | 5 |
| EDTA-3Na•2H2O | 0.1 | 0.1 | 0.1 |
| Dynamite glycerin | 3 | 3 | 3 |
| Ethanol | 5 | 5 | 5 |
| Phenoxyethanol | 0.5 | 0.5 | 0.5 |
| Covering of pigmented spots and freckles | B | B | A |
| Unnoticeableness of pores | D | B | B |
| Natural makeup finish | D | A | B |
| No powderiness | D | B | B |

As shown in Tables 7 and 8, when the commonly-used pigment grade titanium dioxide was blended, covering

TABLE 7

|  | Example | | |
|---|---|---|---|
|  | 1-1 | 1-2 | 1-3 |
| Branched alkyl silicone (ethoxy functional group)-treated talc *1 | Balance | Balance | Balance |
| Zinc decyltrisiloxane carboxylate-treated talc | 12 | 12 | 12 |
| Synthetic fluorine gold mica | 10 | 10 | 10 |
| Dimethicone-treated synthetic fluorine gold mica iron | 10 | 10 | 10 |
| Boron nitride | 5 | 5 | 5 |
| Titanium dioxide (pigment grade) | 7 | — | — |
| The present invention Titanium dioxide | — | 7 | 9 |
| Aluminum stearate-treated titanium dioxide (ultrafine particle) | 4 | 4 | 4 |
| Silicone-treated colcothar | 0.6 | 0.6 | 0.6 |
| Silicone-treated yellow iron oxide | 2.1 | 2.1 | 2.1 |
| Silicone-treated black iron oxide | 0.2 | 0.2 | 0.2 |
| Spherical nylon powder | 5 | 5 | 5 |
| Spherical silicone resin-covered phenyl gum powder | 5 | 5 | 5 |
| Fatty acid dextrin-treated low temperature-calcined zinc oxide | 3 | 3 | 3 |
| Chlorphenesin | 0.2 | 0.2 | 0.2 |
| Dimethicon | 3 | 3 | 3 |
| Methylphenylpolysiloxane | 2 | 2 | 2 |
| Glyceryl tri-2-ethyl hexanoate | 4 | 4 | 4 |
| Octyl methoxycinnamate | 5 | 5 | 5 |
| Covering of pigmented spots and freckles | B | B | A |
| Unnoticeableness of pores | C | A | A |
| Natural makeup finish | C | A | B |
| No powderiness | D | A | B | power was provided, but pores were noticeable and the makeup finish was less natural.

On the other hand, when the titanium dioxide powder according to the present invention was blended, the covering power was provided, and in addition, pores were unnoticeable and the natural makeup finish was also achieved. Further, even when the blending amount was increased, further covering power was provided, and in addition, pores were unnoticeable and the natural makeup finish was also achieved. Moreover, the makeup finish was not powdery.

Hereinafter, formulation examples of cosmetics containing the titanium dioxide of the present invention and production methods of the cosmetics will be described.

[Two-Way Powder Foundation]

| (Formulation) | (% by mass) |
|---|---|
| Dimethicone-treated talc (*1) | To 100 |
| Silicone-treated sericite | 5 |
| Synthetic fluorine gold mica (*2) | 10 |
| Synthetic fluorine gold mica iron | 10 |
| Boron nitride (*3) | 3 |
| Aluminum stearate-treated titanium dioxide (of the present invention) | 10 |
| Dimethicone-treated fine particle titanium dioxide | 6 |
| Dimethicone-treated colcothar | 0.8 |
| Dimethicone-treated yellow iron oxide | 3 |
| Dimethicone-treated black iron oxide | 0.2 |
| Silicone elastomer spherical powder (*4) | 5 |
| Silicone resin-covered silicone elastomer spherical powder (*5) | 5 |
| Dimethicone 6 cs | 3 |
| Methylphenylpolysiloxane | 2 |
| Triethylhexanoin | 1 |
| Sorbitan sesquiisostearate | 1 |
| Octyl methoxycinnamate | 3 |
| Octocrylene | 2 |
| Preservative agent | 0.1 |
| Antioxidant | 0.01 |
| Perfume | 0.01 |

(*1) Miyoshi Kasei Industry Co., Ltd SA-Talc JA68R
(*2) Topy Indusry Co., Ltd PDM-9WA
(*3) Merk Co., Ltd RonaFlair Boroneige SF-12
(*4) Dow Corning Toray Co., Ltd Trefil E506S
(*5) Shin-Etsu Chemical Co., Ltd KSP100

[Production Method]

In a Henschel mixer, the powders and the preservative were mixed with the oil, the antioxidant, and the essence that have been heated at 80° C., which was then pulverized by a pulverizer. A resultant powder was dry press molded in a middle-sized resin dish to produce a dual-purpose powdery foundation.

[Loose Type Foundation]

| (Formulation) | (% by mass %) |
|---|---|
| Magnesium myristate-treated talc | To 100 |
| Mica | 20 |
| Silicone-treated synthetic fluorine gold mica | 20 |
| Boron nitride (*6) | 5 |
| Bismuth oxychloride (*7) | 3 |
| titanium dioxide (The present invention) | 8 |
| Zinc oxide | 3 |
| Stearic acid-treated fine particle titamiun oxide | 6 |
| Spherical silicone powder (*8) | 3 |
| Spherical silica | 3 |
| Spherical polyurethane powder (*9) | 3 |
| Silicone resin-covered silicone elastomer spherical powder (*5) | 3 |
| Silicone-treated colcothar | 0.6 |
| Silicone-treated yellow iron oxide | 2 |
| Silicone-treated black iron oxide | 0.2 |
| Dimethicone 6 cs | 1 |
| Cethyl octanoate | 1 |
| Octyl methoxycinnamate | 2 |
| Preservative agent | 0.2 |
| Antioxidant | 0.05 |
| Perfume | 0.05 |

(*6) Merk Co., Ltd RonaFlair Boroneige SF-12
(*7) Merk Co., Ltd RonaFlair LF-2000
(*8) Momentive Performance Materials Japa, LLC Tospal 145A
(*9) TOSHIKI PIGMENT Co., Ltd Plastic powderD-400

[Production Method]

In a Henschel mixer, the powders and the preservative were mixed with the oil, the antioxidant, and the essence that have been heated at 80° C., which was then pulverized by a pulverizer to produce a foundation in a loose form.

(Water-in-Oil Emulsion Foundation)

| (Formulation) | (% by mass) |
|---|---|
| Oil phase | |
| Decamethyl cyclopentasiloxane | 15 |
| Dimethicone 1.5 cs | 10 |
| Methylphenylpolysiloxane | 3 |
| Triethylhexanoin | 2 |
| Octyl methoxycinnamate | 5 |
| Polyoxyalkylene-modified silicone (*10) | 2 |
| Polyoxyalkylene/alkyl co-modified silicone (*11) | 2 |
| Organic-modified hectorite | 1 |
| Powder | |
| Octyl triethoxysilane-treated titanium dioxide (of the present invention) | 10 |
| Stearic acid-treated fine particle titamiun oxide | 5 |
| Dimethicone-treated colcothar | 0.4 |
| Dimethicone-treated yellow iron oxide | 1.5 |
| Dimethicone-treated black iron oxide | 0.1 |
| Spherical nylon powder | 5 |
| Water phase | |
| Ion-exchanged water | To 100 |
| glycerin | 5 |
| Ethanol | 3 |
| 1,3-buthylene glycol | 5 |
| Phenoxyethanol | 0.5 |

(*10) Shin-Etsu Chemical Co., Ltd KF6017
(*11) Shin-Etsu Chemical Co., Ltd KF6038

[Production Method]

In the oil phase portion, organically modified hectorite was added and mixed with a homogenizer for 1 minute. The powder portion was subsequently added therein and mixed again with a homogenizer for 1 minute. The aqueous phase portion that has been prepared by dissolving was added therein, mixed again with a homogenizer for 1 minute and emulsified to produce a water-in-oil type emulsified foundation.

What is claimed is:

1. A method for producing a titanium dioxide powder, comprising:
   a step of calcining rutile titanium dioxide particles having needle projections on the surfaces thereof; and
   having an average particle size of 100 nm to 600 nm; an average crystallite size of 1 nm to 25 nm; and a specific surface area of 40 $m^2/g$ to 200 $m^2/g$;
   wherein the obtained titanium dioxide powder has an average particle size of 100 nm to 500 nm; an average crystallite size of 15 nm to 30 nm; and a specific surface area of 10 $m^2/g$ to 30 $m^2/g$, and wherein said average particle size is measured using a scale, and said average crystallite size is measured using an X-ray diffraction method.

2. The method for producing a titanium dioxide powder, according to claim 1, wherein:
said calcining is carried out in a temperature range of 500° C. to 700° C.

3. The method for producing a titanium dioxide powder, according to claim 2, wherein:
said step of calcining is performed in a rotary furnace; and
said temperature for said calcining is in the range of 550° to 700° C.

4. The method for producing a titanium dioxide powder, according to claim 3, wherein:
said temperature for said calcining is in the range of 575° to 660° C.

* * * * *